United States Patent [19]

Chan

[11] Patent Number: 5,382,582

[45] Date of Patent: Jan. 17, 1995

[54] METHOTREXATE ANALOGS AND METHODS OF USING SAME

[76] Inventor: Carcy L. Chan, 4113 Sano St., Los Angeles, Calif. 90065

[21] Appl. No.: 37,819

[22] Filed: Mar. 26, 1993

[51] Int. Cl.⁶ ............................................. A61K 31/505
[52] U.S. Cl. ................................ 514/249; 544/260; 544/336
[58] Field of Search ................... 544/260; 514/249; 424/1.1

[56] References Cited

U.S. PATENT DOCUMENTS

| | | |
|---|---|---|
| 2,512,572 | 6/1950 | Smith et al. ........................... 544/260 |
| 3,892,801 | 7/1975 | Kazan . |
| 3,981,983 | 9/1976 | Caston et al. . |
| 3,989,703 | 11/1976 | Niculescu-Duvaz ............... 544/260 |
| 4,043,759 | 8/1977 | Charm et al. . |
| 4,057,548 | 11/1977 | Wiecko ................................ 544/260 |
| 4,067,867 | 1/1978 | Wiecko ................................ 544/260 |
| 4,079,056 | 3/1978 | Piper et al. ........................... 544/260 |
| 4,080,325 | 3/1978 | Ellard .................................. 544/260 |
| 4,093,607 | 6/1978 | Sela et al. . |
| 4,102,455 | 7/1978 | Charm et al. . |
| 4,136,101 | 1/1979 | Kazan . |
| 4,224,446 | 9/1980 | Catalucci ............................. 544/260 |
| 4,279,992 | 7/1981 | Boguslaski et al. ...................... 435/7 |
| 4,306,064 | 12/1981 | Ellard et al. ......................... 544/260 |
| 4,374,987 | 2/1983 | Singh et al. ......................... 544/260 |
| 4,376,767 | 3/1983 | Sloan . |
| 4,378,428 | 3/1983 | Farina et al. ............................ 435/7 |
| 4,401,592 | 8/1983 | Yoshikumi et al. . |
| 4,421,913 | 12/1983 | Ellard et al. ......................... 544/258 |
| 4,489,065 | 12/1984 | Walton et al. ....................... 536/118 |
| 4,622,218 | 11/1986 | Bodor .................................. 514/356 |
| 4,625,014 | 11/1986 | Senter et al. ........................ 530/300 |
| 4,638,045 | 1/1987 | Kohn et al. .......................... 530/323 |
| 4,671,958 | 6/1987 | Rodwell et al. ..................... 530/387 |
| 4,699,784 | 10/1987 | Shih et al. ........................... 530/391 |
| 4,767,859 | 8/1988 | Zimmerman ....................... 544/258 |
| 4,785,080 | 11/1988 | Farina et al. ........................ 530/402 |
| 4,816,395 | 3/1989 | Hancock et al. .................... 436/800 |
| 4,886,780 | 12/1989 | Faulk ...................................... 514/8 |
| 4,918,165 | 4/1990 | Soll et al. ............................ 530/391 |
| 4,925,662 | 5/1990 | Oguchi et al. ...................... 530/391 |
| 4,939,240 | 7/1990 | Chu et al. ............................ 530/387 |
| 4,997,913 | 3/1991 | Hellstrom et al. .................. 530/389 |
| 5,010,103 | 4/1991 | Kalman ............................... 514/495 |
| 5,028,697 | 7/1991 | Johnson et al. ..................... 530/388 |
| 5,030,719 | 7/1991 | Umemoto et al. .................. 530/391 |
| 5,057,313 | 10/1991 | Shih et al. ........................... 530/391 |
| 5,059,413 | 10/1991 | Reardan et al. ..................... 530/391 |
| 5,082,928 | 1/1992 | Best ..................................... 530/391 |
| 5,084,560 | 1/1992 | Hellstrom et al. .................. 530/391 |
| 5,106,950 | 4/1992 | Farina et al. ........................ 530/345 |
| 5,108,987 | 4/1992 | Faulk ...................................... 514/8 |
| 5,196,533 | 3/1993 | Ayling et al. ....................... 544/258 |

OTHER PUBLICATIONS

Chaykovsky et al. Jour Med Chem vol. 17 pp. 1212–1216 (1974).

Taylor et al. Jour. Am. Chem. Soc. vol. 95 pp. 6413–6418 (1973).

Frei III, Spurr, Brindley, Selawry, Holland, Rall, Wasserman, Hoogstraten, Schnider, McIntyre, Matthews Jr., and Miller, "Clinical studies of dichloromethotrexate (NSC 29630)" Clin. Pharmacol. Exp. Ther., 6, 160 (1965).

Rosowsky and Chen, "Methotrexate Analogs. 4.7—Methyl Derivatives of Methotrexate and Dichloromethotrexate. A New Synthesis and Some Biological Studies", J. Med. Chem., 17, 1308 (1974).

Chaykovsky, Brown and Modest, "Methotrexate Analogs. 6. Replacement of Glutamic Acid by Various Amino Acid Esters and Amines", J. Med. Chem., 18, 909 (1975).

(List continued on next page.)

*Primary Examiner*—Donald G. Daus
*Attorney, Agent, or Firm*—Leydig, Voit & Mayer, Ltd.

[57] ABSTRACT

The methotrexate analogs 7-d-MTX, 7,9,9-$d_3$-MTX, MTX halogenated or possessing some other such group at the 7-position capable of reducing oxidation to 7-OH-MTX, and structurally related analogs, as well as pharmaceutical compositions containing the analogs, the synthesis of the MTX analogs, and use of the analogs in modulating cellular function.

21 Claims, No Drawings

OTHER PUBLICATIONS

Chaykovsky, "Direct $N^8$-Alkylation of 2,4-Diamino-7,8-dihydropteridines. Preparation of 7,8-Dihydro-8-Methylmethotrexate", *J. Org. Chem.*, 402, (1), 145 (1975).

Rosowsky and Yu, "Methotrexate Analogues. 10. Direct Coupling of Methotrexate and Diethyl L–Glutamate in the Presence of Peptide Bond–Forming Reagents", *J. Med. Chem.*, 21, 170 (1978).

Rosowsky, Beardsley, Ensminger, Lazarus, and Yu, "Methotrexate Analogues. 11. Unambiguous Chemical Synthesis and in Vitro Biological Evaluation of α–and τ– Monoesters as Potential Prodrugs", *J. Med. Chem.*, 21, 380 (1978).

Kempton, Black, Anstead, Kumar, Blankenship and Freisheim, "Lysine and Ornithine Analogues of Methotrexate as Inhibitors of Dyhydrofolate Reductase", *J. Med. Chem.*, 25, 475–477 (1982).

Henkin and Washtien, "Novel Fluorinated Antifolates. Enzyme Inhibition and Cytotoxicity Studies on 2' and 3'–Fluoroaminopterin", *J. Med. Chem.*, 26, 1193–1196 (1983).

Goldman and Matherly, "The Cellular Pharmacology of Methotrexate", *Pharmac. Ther.*, 28, 77 (1985).

Lopez, Bourdeaux, Chauvet, Gilli, and Briand, "Binding of 7–hydrosy–methotrexate to human serum albumin", *Biochemical Pharmacology*, 35, (16), 2834 (1986).

Furst, Herman, Koehnke, Ericksen, Hash, Riggs, Porras and Veng-Pedersen, "Effect of Aspirin and Sulindac on Methotrexate Clearance", *Journal of Pharmaceutical Sciences*, 79 (9), 782 (1990).

Rosowsky, Wright, Holden and Waxman, "Influence of Lipophilicity And Carboxyl Group Content On The Rate of Hydroxylation of Methotrexate Derivatives By Aldehyde Oxidase", *Biochemical Pharmacology*, 40, 851 (1990).

McGuire, Bolanowska, Coward, Sherwood, Russell and Felschow, "Biochemical and biological properties of methotrexate analogs containing D–glutamic acid or D–erythro, threo–4–fluoroglutamic acid", *Biochemical Pharmacology*, 42 (12), 2400 (1991).

*Cancer Chemotherapy and Biological Response Modifiers Annual 13*, Pinedo et al., eds. (Elsevier Science Publ. B.V., 1992), pp. 1–10, 25–26, 70–74, 119, 138, 140, 144–147.

"Synthesis of a New Analog of Methotrexate and its Inhibitory Effect on Dihydrofolate Reductase," poster presentation at 1992 National Conference on Undergraduate Research (Mar. 27, 1992).

Tomita et al., "Synthesis and in vitro Metabolic Study of d–MTX, a New Analog", poster presentation at NIH Centennial MRRS–MARC Symposium (Oct. 1–3, 1987).

Chan et al., "Synthesis and Metabolic Study of 7,9,9—Trideuteromethotrexate", poster presentation at the *Society for Advancement of Chicanos and Native Americans in Science* (SACNAS) meeting held in Los Angeles, Calif. (Sep. 25–26, 1986).

Goldman, "A Model System For The Study of Heteroexchange Diffusion: Methotrexate–Folate Interactions in L1210 Leukemia and Ehrlich Ascites Tumor Cells", *Biochem Biophys. Acta*, 233, 624–634 (1971).

Goldman, "The Characteristics of the Membrane Transport of Amethopterin and the Naturally Occurring Folates", *Annals New York Academy of Science*, 186, 400–422 (1971).

METHOTREXATE ANALOGS AND METHODS OF USING SAME

FIELD OF THE INVENTION

The present invention relates to novel methotrexate analogs, pharmaceutical compositions containing the analogs, methods of synthesizing the analogs, and methods for their use. In particular, this invention relates to the methotrexate analogs 7-d-MTX, 7,9,9-d$_3$-MTX, MTX possessing a halogen or other such group at the C-7 position capable of reducing oxidation at this site, and structurally related derivatives. These analogs are useful in modulating cellular functions.

BACKGROUND OF THE INVENTION

Within the cell, important molecules called tetrahydrofolates (THF) power the life-sustaining processes of DNA synthesis, replication and repair by coenzymatically providing substrates necessary for these processes. THF are biosynthesized intracellularly through reduction of folic acid or other dihydrofolate intermediates by the enzyme dihydrofolate reductase (DHFR). The pteridine compound, methotrexate (MTX; N-[4-[[(2,4-diamino-6pteridinyl)methyl]methylamino]benzoyl]-L-glutamicacid), is structurally quite similar to folic acid. As a result of this structural similarity, MTX can bind to active sites on DHFR, and, through competitive inhibition, block the formation of THF needed in the biosynthesis of DNA and RNA.

This ability of MTX to inhibit nucleic acid synthesis has been exploited in the treatment of aberrant cell growth. In particular, since many malignant cells proliferate more rapidly than normal cells, and since actively proliferating cells are more sensitive to the effect of MTX, in many cases, MTX can be used to selectively impair cancerous cell growth without damaging normal cell growth. As a result of its effectiveness against rapidly proliferating cells, MTX is one the most widely used anticancer agents. For example, MTX is employed in the treatment of neoplastic diseases such as gestational choriocarcinoma, chorioadenoma destruens, hydatidiform mole, acute lymphocytic leukemia, breast cancer, epidermoid cancers of the head and neck, advanced mycosis fungoides, lung cancer, and non-Hodgkins lymphomas (*Physicians Desk Reference* (45th ed.), Medical Economical Co., Inc., 1185–89 (Des Moines, Iowa (1991))). Moreover, MTX is an effective immunosuppressive agent, with utility in the prevention of the graft-versus-host reaction that can result from tissue transplants, as well as in the management of inflammatory diseases. Consequently, MTX can be employed in the treatment of severe and disabling psoriasis and rheumatoid arthritis (Hoffmeister, *The American Journal of Medicine*, 30, 69–73 (1983); Jaffe, *Arthritis and Rheumatism*, 31, 299 (1988)).

The numerous patents that have been issued disclosing MTX and MTX analogs, methods of synthesizing MTX or analogs thereof, and uses for MTX attest to the significance of MTX in treatment of aberrant cell growth. For example, U.S. Pat. No. 2,512,572 covers the active agent MTX, and U.S. Pat. Nos. 3,892,801, 3,989,703, 4,057,548, 4,067,867, 4,079,056, 4,080,325, 4,136,101, 4,224,446, 4,306,064, 4,374,987, 4,421,913, and 4,767,859 claim methods for preparing MTX or potential intermediates in the synthesis of MTX. Other patents disclose labelled analogs of MTX, such as U.S. Pat. Nos. 3,981,983, 4,043,759, 4,093,607, 4,279,992, 4,376,767, 4,401,592, 4,489,065, 4,622,218, 4,625,014, 4,638,045, 4,671,958, 4,699,784, 4,785,080, 4,816,395, 4,886,780, 4,918,165, 4,925,662, 4,939,240, 4,983,586, 4,997,913, 5,024,998, 5,028,697, 5,030,719, 5,057,313, 5,059,413, 5,082,928, 5,106,950, and 5,108,987, wherein MTX is bound to a radionucleotide or fluorescent label, amino acid, polypeptide, transferrin or ceruloplasmin, chondroitin or chondroitin sulfate, antibody, or binding partner for a specific cell-surface receptor of target cells for use in assays of MTX, in timed-release of MTX, as toxins selective for cancer cells, or to facilitate transport of MTX across membranes or in vivo barriers. Of the numerous patents issued disclosing methods of using MTX, a variety of patents such as U.S. Pat. Nos. 4,106,488, 4,558,690, and 4,662,359 disclose methods of using MTX to treat cancer. Additionally, U.S. Pat. Nos. 4,396,601 and 4,497,796 describe the use of MTX to select cells that have been transfected with vectors containing a DHFR selectable marker, and U.S. Pat. No. 5,043,270 discloses the use of MTX to select for or assess gene amplification events. The basis for these two latter approaches is that an increase in the number of copies of the DHFR gene within a cell correspondingly increases resistance to MTX.

Despite the broad utility and utilization of MTX, treatment with this agent involves a strong risk to the patient. Since MTX interferes with cell replication and division, actively proliferating non-malignant tissues such as bone marrow and intestinal mucosa are more sensitive to MTX and may demonstrate impaired growth due to treatment. More importantly, MTX is associated with renal and hepatic toxicity when applied in the "high dose regimen" that is typically required for maximum efficiency (Barak et al., *J. American Coll. Nutr.*, 3, 93–96 (1984)). It appears that a major metabolite of MTX, 7-OH-MTX, is the source of this toxicity. In both man and monkeys, MTX is converted in vivo to 7-hydroxymethotrexate (7-OH-MTX) (Borsi et al., *Cancer Chemother. Pharmacol.*, 27, 164–67 (1990); Jacobs et al. *J. Clin. Investig.*, 57, 534–38, (1976)). Also, 7-OH-MTX has been found in both urine and plasma samples of patients following high dose MTX therapy (Watson et al., *Cancer Res.*, 43, 4648 (1983); Breithaupt et al., *Cancer Treatment Rep.*, 9, 1733 (1982); Heiko et al., *Pharmacol.*, 26, 138–143 (1990); Chatelut et al., *J. Pharmaceutical Sci.*, 80, 730–34 (1991); Lopez et al., *Biochemical Pharmacol.*, 35, 2834–36 (1986)).

To alleviate MTX-induced toxicity, high dose MTX therapy can be administered in conjunction with citrovorum factor as a "rescue" agent for normal cells (Christenson et al., *J. Clin. Oncol.*, 6, 797–801 (1988)). While citrovorum factor rescue reduces MTX toxicity to non-malignant cells, it does not solve the problem of renal and hepatic impairment due to the formation of 7-OH-MTX.

Because of the undisputed value of MTX in therapy and research, attempts have been made to increase the effectiveness of MTX and decrease the problems attendant with its use. Many investigators have modified the structure of MTX in attempts to synthesize more potent MTX derivatives. The most effective derivatives include aminopterin, which possesses a hydrogen instead of a methyl group at position N-10, and 4-amino derivatives with halogen substitution on the para-aminobenzoic moiety, such as dichloromethotrexate (Frei et al., *Clin. Pharmacol. and Therap.*, 6, 160–71 (1965)). Additional MTX derivatives have been synthesized by: (i)

preparing ester derivatives of the glutamyl moiety, (ii) replacing the glutamic acid with amino acids and peptides, (iii) adding a methyl group at the 7-position, (iv) poly-(L-lysine) conjugation, and (v) substituting the gamma amides (Rosowsky and Yu, *J. Med. Chem.*, 21, 170–75 (1978); Rosowsky et al., *J. Med. Chem.*, 21, 380–86 (1978); Chaykovsky et al., *J. Med. Chem.*, 18, 909–12 (1975); Rosowsky and Chen, *J. Med. Chem.*, 18, 1308–11 (1974)). More recent modification attempts include the synthesis of lysine and ornithine derivatives of MTX (Kempton et al., *J. Med Chem.*, 25, 475–477 (1982); Patil et al., *J. Med. Chem.*, 32, 1559–65 (1989)). These attempts to improve the efficacy of MTX have not yet proven entirely successful. Whereas some of the MTX derivatives, like 7-methyl substituted MTX (Rosowsky and Chen, *J. Med. Chem.*, 18, 1308–11 (1974)), demonstrate impaired antifolate antagonism, others, such as 3', 5'-difluoro MTX, demonstrate little or no increase in biological activity as compared with MTX (Tomcuf, *J. Organic Chem.*, 26, 3351 (1961)). Still other derivatives, like the 2' and 3' monoflourinated derivatives of aminopterin, appear promising, but animal studies remain to be performed (Henkin and Washtien, *J. Med. Chem.*, 26, 1193–1196 (1983)). Similarly, 7,8-dihydro-8-methyl-MTX has been prepared, but the biological properties of this and other compounds remain to be fully investigated (Chaykovsky, *J. Org. Chem.*, 40 (1), 145–146 (1975) ).

Consequently, there remains a need for MTX derivatives having improved or at least equivalent efficacy as MTX and having reduced toxicity for normal cells. One study investigated the influence of lipophilicity and carboxyl group content on the ability of MTX derivatives to undergo 7-hydroxylation in vitro (Rosowsky et al., *Biochem. Pharmacol.*, 40, 851–857 (1990)). While increasing lipophilicity was found to facilitate hydroxylation, the addition of two to five poly-glutamyl residues to the MTX molecule caused a decrease in the rate of hydroxylation at the 7-position. However, this study did not determine the effectiveness of the glutamylated derivatives at inhibiting DHFR. Thus, it is an object of the present invention to provide MTX derivatives that compare with MTX in ability to inhibit DHFR and demonstrate reduced hydroxylation at the C-7 position.

In particular, it is an object of the present invention to provide novel analogs of MTX which modulate at least one cellular function, such as DHFR-mediation of DNA synthesis or repair, and show reduced hydroxylation at the 7-position, as compared with MTX. It is an additional object of the present invention to provide pharmaceutical compositions comprising therapeutically acceptable excipients and novel analogs of MTX. It is a further object of the present invention to provide methods of synthesizing such novel analogs of MTX and methods of modulating at least one cellular function using such novel analogs of MTX.

These and other objects and advantages of the present invention, as well as additional inventive features, will be apparent from the description of the invention provided herein.

BRIEF SUMMARY OF THE INVENTION

The present invention relates to methotrexate analogs, pharmaceutical compositions containing the analogs, methods of synthesizing the analogs, and methods for their use. In particular, this invention relates to the methotrexate analogs 7-d-MTX, 7,9,9-d$_3$-MTX, MTX possessing a halogen or other such group at the C-7 position capable of reducing oxidation at this site, and structurally related derivatives. These analogs are useful in the modulation of cellular function in much the same manner as MTX, yet exhibit reduced 7-hydroxylation as compared to MTX.

DESCRIPTION OF THE PREFERRED EMBODIMENTS

The present invention concerns novel methotrexate analogs, pharmaceutical compositions containing the analogs, methods of synthesizing the analogs, and methods for their use.

The present invention involves MTX analogs capable of functioning as effective folate antagonists and having potentially reduced renal and hepatic toxicity as compared with MTX. These novel analogs were developed based on the premise that since formation of the toxic metabolite 7-OH-MTX occurs through hydroxylation of the 7-position of MTX, inhibition of oxidation at this position can be employed to decrease or block the formation of 7-OH-MTX. Inhibition of oxidation is accomplished in the context of the present invention by increasing the strength of the bond between C-7 and its substituent. In particular, the present inventive compounds reduce oxidation at the 7-position by replacing the hydrogen bonded at C-7 with an atom that binds more tightly, such as deuterium, a halogen, or other such group that will decrease the oxidation at the 7-position as compared to unmodified methotrexate. The MTX analogs contemplated in the context of the present invention have approximately equivalent or slightly greater antifolate activity than MTX, and can replace MTX in its applications, thus reducing renal and hepatic toxicity while maintaining desired efficacy.

The methotrexate analogs of the present invention have the general structure indicated below:

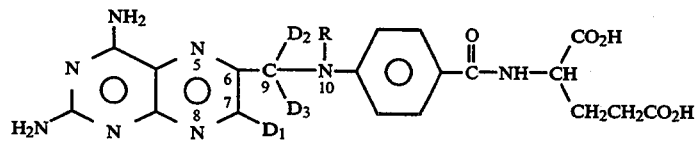

wherein R is methyl or hydro, $D_1$ is deutero or halo, or some other such group capable of decreasing oxidation at the $D_1$ position relative to unmodified methotrexate, and $D_2$ and $D_3$ are individually deutero or hydro, as well as therapeutically acceptable analogs, derivatives, and salts thereof. The methotrexate analogs utilized in the context of the present invention are preferably: 7-d-MTX, which possesses methyl at R, deuterium at $D_1$, and hydrogen at $D_2$ and $D_3$; and 7,9,9-d$_3$-MTX, which possesses methyl at R and deuterium at $D_1$, $D_2$ and $D_3$. Other preferred methotrexate analogs are similar to 7,9,9-d$_3$-MTX and 7-d-MTX, wherein R is a hydrogen substituted at position N-10, such as is found in the folate antagonist aminopterin, instead of the methyl group that is present at this position in MTX. Moreover, the MTX analogs of the present invention may possess halogen substitution on the para-aminobenzoic moiety. Additionally, since long chain polyglutamyl derivatives of MTX enhance intracellular retention of the drug and are also inhibitory to other folate requiring enzymes (U.S. Pat. No. 5,010,103), the present novel analogs may be polyglutamylated.

The present invention contemplates as active agents those analogs of MTX that have been modified such that the C-7 carbon of MTX is refractory to hydroxylation. In particular, the approach contemplates as active agents 7-d-MTX, 7,9,9-d$_3$-MTX, MTX halogenated on the C-7 carbon, MTX possessing other groups at the C-7 carbon capable of reducing oxidation at this site, and therapeutically acceptable analogs, derivatives, and salts of these active agents. The MTX analogs of the present invention may be used alone or in association with other suitable compounds and carriers, and also may be used in combination with other active agents.

The present invention, therefore, also includes pharmaceutical compositions comprising pharmaceutically active excipients and an active agent, where the active agent is an analog of MTX modified to reduce hydroxylation at the C-7 carbon. In particular, the approach contemplates as active agents 7-d-MTX, 7,9,9-d$_3$-MTX, MTX halogenated on the C-7 carbon, MTX possessing other groups at the C-7 carbon capable of reducing oxidation at this site, and therapeutically acceptable derivatives and salts of these active agents. The active agent may be present in the pharmaceutical composition in any suitable quantity. The pharmaceutically acceptable excipients include, for example, any suitable vehicles, adjuvants, carriers or diluents, and are readily available to the public. The pharmaceutical compositions of the present invention may further contain other active agents as are well known in the art.

The present invention provides methods of synthesizing the MTX analogs of the present invention, particularly the preferred analogs 7-d-MTX and 7,9,9-d$_3$-MTX. MTX halogenated on the C-7 carbon, MTX possessing other groups at the C-7 carbon capable of reducing oxidation at this site, and additional modifications to MTX, such as replacement of the methyl group present on N-10 in MTX with a hydrogen, and therapeutically acceptable derivatives of the active agents contemplated, can also be synthesized through modifications to the procedural approaches described herein for 7-d-MTX and 7,9,9-d$_3$-MTX, such modifications being well known to those of ordinary skill in the art.

The method of synthesizing an active agent which is an analog of MTX substituted at the C-7 carbon comprises reacting substrate with chlorine, deuterium oxide and NaNO$_2$, reacting the obtained product of this reaction with aminomalononitrile tosylate, reacting the obtained product with phosphorus trichloride, reacting the obtained product with 4-(N-methylamino) benzoic acid and diisopropyl ethylamine, reacting the obtained product with an ethanol solution of guanidine hydrochloride and sodium ethoxide from which solid NaCl has been removed, reacting the obtained product with a solution of triethylamino and diethyl cyanophosphate in DMF, to which Et$_3$N and diethyl L-glutamate or di-t-butyl-L-glutamate have been added, and reacting the obtained product with an alkaline solution or trifluoroacetic acid to form a precipitate of this active agent.

An alternative synthesis comprises reacting substrate with chlorine, deuterium oxide and NaNO$_2$, reacting the obtained product of this reaction with aminomalononitrile tosylate, reacting the obtained product with phosphorus trichloride, reacting the obtained product with diethyl p-methylaminobenzoyl glutamate and potassium carbonate, reacting the obtained product with an ethanol solution of guanidine hydrochloride and sodium ethoxide from which solid NaCl has been removed, and reacting the obtained product with an alkaline solution to form a precipitate of the active agent.

The method of synthesizing 7-d-MTX comprises (a) reacting diketene with chlorine to yield 4-chloro-3-oxobutanoyl chloride; (b) reacting 4-chloro-3-oxobutanoyl chloride with deuterium oxide and then NaNO$_2$ to form 1-chloro-3-deuterooximino-2-propanone; (c) reacting 1-chloro-3-deuterooximino-2-propanone with aminomalononitrile tosylate to form 2-amino-3-cyano-5-chloromethyl-6-deuteropyrazine-1-oxide; (d) reacting 2-amino-3-cyano-5-chloromethyl-6-deuteropyrazine-1-oxide with phosphorus trichloride to form 2-amino-3-cyano-5-chloromethyl-6-deuteropyrazine; (e) reacting 2-amino-3-cyano-5-chloromethyl-6-deuteropyrazine with 4-(N-methylamino) benzoic acid and diisopropyl ethylamine to form 4-[[(2-amino-3-cyano-6 deuteropyrazin-5-yl) methyl]methylamino]benzoic acid; (f) reacting 4-[[(2-amino-3-cyano-6 deuteropyrazin-5-yl) methyl]methylamino]benzoic acid with an ethanol solution of guanidine hydrochloride and sodium ethoxide from which solid NaCl is removed to form 4-[[(4-amino-7-deuteropteridine-6-yl) methyl]-methylamino]benzoic acid; (g) reacting 4-[[(4-amino-7-deuteropteridine-6-yl) methyl]-methylamino]-benzoic acid with a solution of triethylamino and diethyl cyanophosphate in DMF, to which Et$_3$N and diethyl L-glutamate or di-t-butyl-L-glutamate are added to form a diethyl ester of 7-deuteromethotrexate or di-t-butyl ester of 7-deuteromethotrexate; and (h) dissolving the ester in ethanol and adding an alkaline solution or trifluoroacetic acid to form a precipitate of 7-d-MTX.

The method of synthesizing 7,7,9-d$_3$-MTX involves a somewhat different synthesis route and comprises (a) preparing liquid diketene-d4 from acetone-d6; (b) reacting diketene-d4 with chlorine to yield 4-chloro-3-oxobutanoyl chloride; (c) reacting 4-chloro-3-oxo-butanoyl chloride with deuterium oxide and NaNO$_2$ to form β-chloropyruvaldoxime-d4; (d) reacting β-chloropyruvaldoximed-4 with aminomalononitrile tosylate to form 2-amino-3-cyano-5-chloromethylpyrazine-1-oxide-d3; (e) reacting 2-amino-3-cyano-5-chloromethylpyrazine-1-oxide-d3 with phosphorus trichloride to form 2-amino-3-cyano-5-chloromethylpyrazine-d3; (f) reacting 2-amino-3-cyano-5-chloromethylpyrazine-d3 with diethyl p-methylaminobenzoyl glutamate and potassium carbonate to form diethyl N-[(2-amino-3-cyano-5-methylen(d2)-6-deuteropyrazinyl) methylaminobenzoyl]-glutamate; (g) reacting diethyl N-[(2-amino-3-cyano-5-methylen(d2)-6-deuteropyrazinyl) methylaminobenzoyl]-glutamate with an ethanol solution of guanidine hydrochloride and sodium ethoxide from which solid NaCl is removed to form diethyl-N-[p-[N-(2,4 diamino-7-deutero-6-pteridinyl-9,9-dideuteromethyl)-N -methylamino]-benzoyl]glutamate; and (h) dissolving diethyl-N-[p-[N-(2,4 diamino-7-deutero-6-pteridinyl-9,9-dideuteromethyl)-N-methylamino]-benzoyl]glutamate in ethanol and adding an alkaline solution to form a precipitate of 7,7,9-d$_3$-MTX.

The present invention further includes a method of modulating at least one cellular function, such as DHFR mediation of DNA synthesis or repair, by contacting cells with one of the active agents of the present invention, wherein the active agent is an analog of MTX modified to reduce hydroxylation at the C-7 carbon. In particular, the approach contemplates modulation of a cellular function by the active agents 7-d-MTX, 7,9,9-d$_3$-MTX, MTX halogenated on the C-7 carbon, MTX possessing other groups at the C-7 carbon capable of reducing oxidation at this site, and therapeutically acceptable derivatives and salts of these active agents. The present inventive MTX analogs can be used in place of MTX for all applications of MTX ranging from use as a rodenticide to selecting for gene amplification events. Use of the MTX analogs of the present invention is of particular utility in, for example, the treatment of cancer, psoriasis, rheumatoid arthritis, and tissue-graft rejection, as well as in conditions requiring immunosuppressive agents. In these capacities, use of the present inventive MTX analogs will result in a reduced rate of formation of the toxic compound 7-OH-MTX that results from breakdown of MTX, and will thus reduce MTX-mediated toxicity.

As regards these applications, the present inventive method includes the administration to an animal, particularly a human, of a therapeutically effective amount of one or more of the aforementioned MTX analogs as an active agent effective in the competitive inhibition of DHFR, particularly an active agent selected from the group consisting of analogs possessing a deuterium, halogen, or other such group at the C-7 position capable of reducing oxidation of MTX, and pharmaceutically acceptable derivatives and salts thereof.

One skilled in the art will appreciate that a variety of suitable methods of administering a compound of the present invention to an animal are available, and, although more than one route can be used to administer a particular compound, a particular route can provide a more immediate and more effective reaction than another route. Pharmaceutically acceptable excipients are also well-known to those who are skilled in the art, and are readily available. The choice of excipient will be determined in part by the particular compound, as well as by the particular method used to administer the composition. Accordingly, there is a wide variety of suitable formulations of the pharmaceutical composition of the present invention. The following methods and excipients are merely exemplary and are in no way limiting. However, pharmaceutically acceptable excipients which do not interfere with the inhibition of DHFR are preferred.

Formulations suitable for oral administration can consist of (a) liquid solutions, such as an effective amount of the compound dissolved in diluents, such as water, saline, or orange juice; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The MTX analogs of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Formulations suitable for topical administration may be presented as creams, gels, pastes, or foams, containing, in addition to the active ingredient, such carriers as are known in the art to be appropriate.

Additionally, the MTX analogs employed in the present invention may be made into suppositories by mixing with a variety of bases such as emulsifying bases or water-soluble bases. Formulations suitable for vaginal administration may be presented as pessaries, tampons, creams, gels, pastes, foams.

The dose administered to an animal, particularly a human, in the context of the present invention should be sufficient to effect a prophylactic or therapeutic response in the animal over a reasonable time frame. One skilled in the art will recognize that dosage will depend upon a variety of factors including the strength of the particular compound employed, the condition of the animal, the body weight of the animal, as well as the severity of the illness and the stage of the disease. The size of the dose will also be determined by the existence, nature, and extent of any adverse side-effects that might accompany the administration of a particular compound. Suitable doses and dosage regimens can be determined by comparisons to anticancer or immunosuppressive agents that are known to effect the desired growth inhibitory or immunosuppressive response, particularly unmodified methotrexate. The preferred dosage is the amount which results in inhibition of DHFR, without significant side effects. In proper doses and with suitable administration of certain compounds, the present invention provides for a wide range of intracellular effects, e.g., from partial inhibition to essentially complete inhibition of DHFR. This is especially important in the context of the present invention, as this differential inhibition can potentially be used to discriminate between cancer cells and highly proliferative non-malignant cells.

In the treatment of some individuals with the compounds of the present invention, it may be desirable to use a high dose regimen in conjunction with citrovorum factor rescue of non-malignant cells. In such treatment, any agent capable of rescue of non-malignant cells can be employed, such as citrovorum factor, folate derivatives, or leucovorin. Such rescue agents are well-known to those of ordinary skill in the art. A rescue agent is preferred which does not interfere with the ability of the present inventive compounds to modulate cellular function.

While the examples provided herein involve the synthesis and use of 7-substituted analogs of MTX, the examples do not exclude additional modifications to MTX, for example, such as replacement of the methyl group present on N-10 in MTX with a hydrogen, as is observed for the MTX analog, aminopterin, or halogen substitution on the para-aminobenzoic moiety. Similarly, while the modifications described herein entail deuteration of the 7-position, the present invention also contemplates alternative modifications that would reduce hydroxylation at the C-7 carbon of MTX, such as halogenation of this carbon. Simple modifications of the procedures described herein, such modifications which are well known to those of ordinary skill in the art, would result in halogenation of the C-7 carbon. Similarly, other procedural modifications, also which are well known to those of ordinary skill in the art, would allow modifications to be made at positions in MTX other than the ones described, while maintaining or effecting the 7-substitutions described herein.

The following examples further illustrate the present invention and should not be construed as in any way limiting its scope.

EXAMPLES

The following experimental supplies and instruments were employed in carrying out the experiments which form the examples described herein.

NADPH, dihydrofolic acid, L-amethopterine, and chicken liver DHFR were purchased from Sigma Chemical Co. (St. Louis, MO). MTX was either purchased from Sigma or obtained from the National Institutes of Health (Chemotherapeutic Agents Repository, c/o ERC BioServices Corporation, 1592-E Rockville Pike, Rockville, MD). Partially purified DHFR from MTX-resistant *L. casei* was obtained from the New England Enzyme Center (Boston, MA). 7-OH-MTX, used as a standard solution, and diethyl-p-methylaminobenzoyl glutamate were synthesized from p-methylaminobenzoic acid according to previously described methods (Fu et al., *J. Org. Chem.*, 30, 1277 (1965)). While 7-OH-MTX has been reported to be collected from the rabbit after high dose MTX treatment, this compound was synthesized to ensure purity and authenticity.

Infrared (IR) spectra were recorded on a Beckman 4250 spectrophotometer. $^1$H nuclear magnetic resonance spectro-scopy was conducted with use of a 90-MHz Varian 360 spectrophotometer. High performance liquid chromatography (HPLC) was carried out with use of a Beckman gradient HPLC system. The chromatographic system consisted of a C-R5A chromatopac, SCL-9a system controller and SIL-9A autoinjector. A Shimadzu LC-9A solvent system and a SPD-9AUV spectrophotometric detector were used unless indicated otherwise. Mass spectra were recorded at the University of California (Riverside, CA). Elemental analysis were performed by Galbraith Laboratories, Inc. (Knoxville, TN).

EXAMPLE 1

This example outlines the method of synthesizing MTX analogs possessing some atom other than hydrogen linked to the C-7 position of MTX by presenting the synthesis of 7-d-MTX. This synthesis entails a multistep process which results in the substitution of a deuterium atom for hydrogen at the 7-position of MTX.

Synthesis of 1-chloro-3-deuterooximino-2-propanone.

A solution of 33.6 g of freshly distilled diketene in 300 ml of dry $CCl_4$ along with a magnetic stirring bar was placed in a 500 ml three-neck flask equipped with a thermometer, gas inlet tube and drying tube. The flask was weighed and placed in a dry ice-acetone bath. While the temperature of the solution was maintained at about 0° C. 28.4 g of chlorine was bubbled into the solution with constant stirring. Reaction of the solution with the appropriate weight of chlorine was verified by weighing of the flask. Following this reaction, $CCl_4$ was removed from the solution with use of a rotary evaporator, and the resulting residue was dissolved into 300 ml of dry ether.

In the next step of the synthesis, 300 ml of $D_2O$ (99.9 atomic percent D) was placed in a 1 liter, three-neck flask which was cooled to 4° C. in a dry ice-salt bath. The ether solution of 4-chloro-3-oxo-butanoyl chloride was added dropwise with constant stirring while the temperature was maintained below 5° C. Following addition of the 300 ml of ether solution, the two-phase mixture was stirred for 24 hours at about 4° C. Then 27.6 g of $NaNO_2$ was added in small aliquots with constant stirring. When addition was completed, the reaction mixture was stirred an additional 15 minutes at room temperature. The solution layers were allowed to separate, and the aqueous layer was extracted with three 50 ml aliquots of ether. The extractions were combined and dried over $Na_2SO_4$. The dried solution was then concentrated using a rotary evaporator, and a cream-colored, waxy-appearing solid was obtained.

1-chloro-3-deuterooximino-2-propanone was further purified by crystallization to give 29 g (60%) of white plates. The resultant 1-chloro-3-deuterooximino-2-propanone had a melting point of about 98°–102° C. The IR spectrum of 1-chloro-3-deuterooximino-2-propanone showed absorptions at 3297, 2993.2 and 1688.9 $cm^1$, corresponding to —OH, CH and C=O conjugated with oxime signals, respectively. The compound showed a nmr singlet at 4.78 (s, —$CH_2Cl$) ppm only, and the nmr spectrum differed from that obtained for 1-chloro-3-oximino-2-propanone. The nmr spectrum confirmed the oxime structure and absence of protons at the 3-carbon of 1-chloro-3-deuterooximino-2-propanone.

Synthesis of 2-amino-3-cyano-5-chloromethyl-6-deuteropyrazine-1-oxide.

A solution of 5.0 g of 1-chloro-3-deuterooximino-2-propanone and 10.7 g of aminomalononitrile tosylate in 140 ml of 2-propanol was stirred at room temperature for 24 hours. The resulting dark red solution was concentrated by evaporation, and 100 ml of water was added. The solution was extracted with four 50 ml aliquots of methylene chloride, the extracts were dried over $Na_2SO_4$ and evaporated to dryness. The resulting residue was dissolved in 50 ml of chloroform and re-crystallized to give 4.2 g, or a 56% yield, of 2-amino-3- cyano-5-chloromethyl-6-deutero-pyrazine-1-oxide. This bright yellow microcrystalline solid had a melting point of 141°–143° C. The IR spectrum of 2-amino-3-cyano-5-chloromethyl-6-deutero-pyrazine-1-oxide showed absorptions at 3390–3280, 2240 and 1635 cm¹, corresponding to $NH_2$, CN, and C=N signals, respectively. The nmr spectrum revealed signals at 4.70 (2,s, —$CH_2Cl$) and 7.70 (2,b,-$NH_2$) ppm. The FAB mass spectrum showed a protonated molecular ion peak at m/z 186. This peak confirmed that the molecular weight of this compound was 185.

Synthesis of 2-amino-3-cyano-5-chloromethyl-6-deuteropyrazine.

A solution of 4.0 g of 2-amino-3-cyano-5-chloromethyl-6-deutero-pyrazine 1-oxide in 150 ml of freshly distilled tetrahydrofuran (THF) was added dropwise to 8.0 g of phosphorus trichloride while cooled in an iced bath. The solution was stirred for 45 min at room temperature. Following evaporation of the solution to a small volume, 100 ml of ice-cold water was added, resulting in the formation of a precipitate. The precipitate was collected by filtration and washed with water to give 2.8 g, or a 78% yield, of a yellow microcrystalline solid of 2-amino-3-cyano-5-chloromethyl-6-deuteropyrazine, having a melting point of 151°–154° C. The IR spectrum of this compound showed absorptions at 3430–3210 and 2240 cm¹, corresponding to $NH_2$ and CN signals, respectively. The nmr spectrum showed signals at 4.57 (2,s,—$CH_2Cl$) and 7.35 (2,b,-$NH_2$) ppm. The FAB mass spectrum showed a protonated molecular ion peak at m/z 170. This peak confirmed that the molecular weight of this compound was 169.

Synthesis of 4-[[(2-amino-3-cyano-6-deuteropyrazin-5-yl) methyl]methylamino]benzoic acid.

A total of 3 g of 2-amino-3-cyano-5-chloromethyl-6-deuteropyrazine was added in small portions with constant stirring to a solution comprised of 2.7 g of 4-(N-methylamino) benzoic acid and 6.2 ml of diisopropyl ethylamine in 35 ml of dry DMF. The resulting mixture was stirred for 1.5 hours at room temperature. The solution was concentrated under reduced pressure to a volume of about 5 ml, following which 200 ml of water and 1 ml of 2M HCl were added. The mixture was stirred for 5 minutes, and the resulting precipitate was collected and added to 100 ml of water. Concentrated $NH_4OH$ was added to dissolve the solid, and the undissolved material was filtered off. The filtrate was acidified with glacial acetic acid to pH 4–5, and the precipitate which formed upon acidification was collected, washed with water and methanol, and air-dried overnight. A 65% yield, or 3.2 g of 4-[[(2-amino-3-cyano-6-deuteropyrazin-5-yl)methyl]methylamino]benzoic acid was obtained. This compound had a melting point of 253°–255° C., and demonstrated IR absorptions at 3400–3200, 2600–2900, 2245 and 1680 cm¹, corresponding to $NH_2$, COOH, CN and COOH signals, respectively. The nmr spectrum for this compound showed signals at 3.03 (s, Me), 4.52 (s,$CH_2$), 6.70 (d, 3'-and 5'-H, J=9Hz), 7.20 (b, NH2), and 7.70 (d,2'-and 6'H, J=9Hz) ppm. The FAB mass spectrum showed a protonated molecular ion peak at m/z 285. This peak confirmed that the molecular weight of this compound was 284.

Synthesis of 4-[[4-amino-7-deuteropteridine-6-yl) methyl]methylamino]benzoic acid.

A solution of 0.6 g of guanidine hydrochloride in 25 ml of absolute ethanol was added to a solution of sodium ethoxide prepared by reacting 0.26 g of sodium metal with 25 ml of absolute ethanol. After 15 minutes, the NaCl precipitate was filtered off, and 1.42 g of 4-[[(2-amino-3-cyano-6 deuteropyrazin-5-yl)methyl]methylamino]benzoic acid was added to the filtrate. The mixture was refluxed for 2 hours and then concentrated to a small volume. The residue was dissolved in 200 ml of water and filtered to yield a clear solution. The solution was acidified to pH 4–5 with glacial acetic acid, and the precipitate formed upon acidification was collected. The precipitate was sequentially washed with $H_2O$, ethanol and ether, and was dried in a desiccator. A yield of 1.6 g of 4-[[4-amino-7-deuteropteridine-6-yl)-methyl]methylamino]benzoic acid was obtained as yellow solid. This compound had a melting point greater than 300° C., and its IR spectrum showed absorptions at 3460–3200, 2940, 1670, 1615, and 1595 cm¹, corresponding to $NH_2$, CH, COOH, C=C, and CN signals. The nmr spectrum showed signals at 3.30 (s, Me), 4.90 (s, $CH_2$), 6.80 (d,3'-and 5'-H, J=9Hz), 7.70 (d,2'-and 4'-H, J=9Hz) and 7.35 (b,$NH_2$) ppm. The compound had a retention time of 9.75 min upon HPLC analysis. HPLC analysis was performed using a $C_{18}$ column. The column was eluted with 27% MeOH in a 0.1 M Tris buffer of pH 6.7 at a flow rate of 1.5 ml/minute. The FAB mass spectrum showed a protonated molecular ion peak at m/z 327. This peak confirmed that the molecular weight of this compound was 326.

Synthesis of a diethylester of 7-deuteromethotrexate.

A total of 0.65 g of 4-[[4-amino-7-deuteropteridine-6-yl)methyl]-methylamino]benzoic acid was added in small aliquots with continuous stirring to a solution comprised of 0.61 g of triethylamino cyanophosphate and 1.0 g of diethyl cyanophosphate in 50 ml of DMF. When the solid dissolved, the mixture was heated to 80° C. for 2 minutes, and then cooled to room temperature. To the cooled solution, 0.2 g of $Et_3N$ and 0.48 g of diethyl-L-glutamate were added, and heating was resumed at 80° C. for 2 hours. The solvent was then evaporated under reduced pressure. The resulting residue was dissolved in 50 ml of $CHCl_3$ and washed with 5% $NaHCO_3$. The $CHCl_3$ layer was eluted and dried over anhydrous sodium sulfate, and then the $CHCl_3$ was evaporated. The resulting residue was dissolved in a small volume of 1:5 EtOH-$CHCl_3$, and the crude diethylester of 7-deuteromethotrexate was chromatographed on a silica gel column (75g, 2.5×60 cm). The column was eluted with 1:5 EtOH-$CHCl_3$, and fractions were collected. The fractions containing diethyl methotrexate were combined, and the solvent was evaporated to give 0.4 g, or a 35% yield, of a light yellow solid of diethylester of 7-deuteromethotrexate. The diethylester had a melting point of 145°–147° C. The IR spectrum of the diethylester showed absorptions at 3400–3200 and 1750 cm¹, corresponding to $NH_2$ and C=O signals, respectively. The nmr spectrum showed signals at 8.25 (1,d,CONH), 7.70 (2,d,aromatic H), 7.35 (2,b,$NH_2$), 6.80 (2,d,aromatic H) , 6.60 (2,b,s,$NH_2$) , 4.75 (2,s,—$CH_2n$) , 4.4 (1,mm,—NCH—) , 4.15 (4,t,—$COOCH_2CH_3$) , 3.20 (3,s,$NCH_3$) , 2.50 and 2.10 (2,m—$CH_2$—$CH_2$—) , and 1.20 (6,t,—$OCH_2CH_3$) ppm. The FAB mass spectrum showed a protonated molecular ion peak at m/z 512.

This peak indicated that the molecular weight of this compound was 511. The structure was confirmed by considering together the fragments m/z 349, 309, and 177.

A similar procedure was used for synthesis of the di-t-butyl ester of 7-d-MTX.

Synthesis of N-{p-[N,(2,4-Diamino-7-deutero-6-pterridinylmethyl)-N-methylamino]benzoyl}-L-glutamic acid, or 7-d-MTX.

While stirring, 10 ml of 2M NaOH was added to 0.8 g of the diethylester of 7-deuteromethotrexate dissolved in 100 ml of ethanol. The solution was protected from light, and was stirred for 24 hours at room temperature under $N_2$ gas. The precipitate formed was collected by filtration and was washed with ethanol. The resulting crude sodium salt of N-{p-[N-(2,4-diamino-7-deutero-6-pterridinylmethyl)-N-methylamino]benzoyl}-L -glutamic acid, or 7-d-MTX, was dissolved in 50 ml of water and filtered. The filtrate was acidified to pH 4 with 1 M HCl, and the mixture was stored in the refrigerator overnight. The bright yellow solid formed was collected and dried to give 0.76 g, or a 95% yield, of 7-d-MTX. The compound had a melting point of 195°–197° C. Elemental analysis of 7-d-MTX confirmed a carbon content of 48.9%, hydrogen content of 5.5%, nitrogen content of 22.8% and oxygen content of 22.8%. Analytical results obtained were within $+/-$ 0.4% of theoretical values. The infrared spectrum of 7-d-MTX showed absorptions at 3400–3000, 2950, 1700, 1635, and 1570 cm−1, corresponding to $NH_2$, CH, COOH, C=C, and C=N signals, respectively. The nmr spectrum showed signals at 8.10 (1,d,—CONHO), 7.60 (2,d,aromatic H), 6.70 (2,d,aromatic H), 7.40 (2,br,s,$NH_2$), 6.50 (2,br,s,$NH_2$), 4.70 (2,s,$CH_2$-N), 4.40 (1,m, CONCH), 3.20 (3,s, N-$CH_3$), 2.40 and 2.10 (2,m,$CH_2$—$CH_2$) ppm. The FAB mass spectrum showed a protonated molecular ion peak at m/z 456. This peak confirmed that the molecular weight of this compound was 455.

EXAMPLE 2

This example outlines the method of synthesizing MTX analogs possessing some atom other than hydrogen linked to the C-7 position of MTX in conjunction with other substitutions by presenting the synthesis of 7,9,9-$d_3$-MTX. This synthesis entails a multi-step process which results in the incorporation of deuterium at the 7- and 9-positions of the molecule.

Synthesis of diketene-d4.

Diketene-d4 was prepared by a previously described method (Williams et al., *J. Org. Chem.*, 5, 122 (1940)), using acetone-d6 as the starting material. The deuterated ketene gas formed from acetone-d6 in the specially-designed generator was collected in a series of cold traps maintained at −78° C. The solution in the traps was gradually allowed to reach room temperature over a period of 24 hours, and was collected and vacuum distilled at 30° C. under low pressure. The resulting residue was heated under atmospheric pressure in a boiling water bath. When the temperature of the residue reached 100° C., the vacuum system was turned on and diketene-d4 was collected at 67°–69° C./92 mm. The crude product obtained was redistilled under atmospheric pressure, and the 124°–127° C. fraction was collected. A 30% yield of diketene-d4 was collected as a lachrymatory, colorless liquid, and was immediately used for the next step of the synthesis.

Synthesis of β-chloropyruvaldoxime-d4.

A solution of 16.8 g of freshly distilled diketene-d4 and 150 ml of dry $CCl_4$, as well as a magnetic stirring bar, was placed in a 250 ml three-neck flask equipped with a thermometer, gas inlet tube and drying tube. The flask was weighed and placed in a dry ice-acetone bath. While the temperature of the solution was maintained at about −5° C. 14 2 g of chlorine was bubbled into the solution with constant stirring. Reaction of the solution with the appropriate weight of chlorine was verified by weighing of the flask. Following this reaction, $CCl_4$ was removed from the solution with use of a rotary evaporator, and the resulting residue was dissolved in 150 ml of dry ether.

In the next step of the synthesis, the ether solution was added dropwise with constant stirring to 13.8 g of $NaNO_2$ in 150 ml of $D_2O$ while the temperature was maintained below 5° C. Following addition of the 150 ml of ether solution, the mixture was stirred 15 minutes at room temperature. The solution layers were allowed to separate, and the aqueous layer was extracted with three 25 ml aliquots of ether. The extractions were combined and dried over $Na_2SO_4$. The dried solution was then concentrated using a rotary evaporator, and a cream-colored waxy-appearance solid was obtained. β-chloropyruvaldoxime-d4 was further purified by crystallization to give 10.5 g, or a 54% yield, of white plates. The resultant β-chloropyruvaldoxime-d4 had a melting point of about 98°–102° C. The IR spectrum of β-chloropyruvaldoxime-d4 showed absorptions at 3200, 1720 and 1620 $cm^1$, corresponding to OH, ketone C=O, and C=N signals respectively. While undeuterated β-chloropyruvaldoxime showed nmr signals at 4.78 (2,s, for —$CH_2Cl$), 7.65 (1,s, for CH=NOH), and 12.75 (1,s, for =NOH) ppm, the synthesized β-chloropyruvaldoxime-d4 did not demonstrate any signal.

Synthesis of 2-amino-3-cyano-5-chloromethylpyrazine-1-oxide-d3.

A solution of 5.0 g of β-chloropyruvaldoxime-d4 and 10.7 g of aminomalononitrile tosylate in 140 ml of 2-propanol was stirred at room temperature for 24 hours. The resulting dark red solution was concentrated by evaporation, and 100 ml of water was added. The solution was then extracted with three 50 ml aliquots of methylene chloride, and the extracts were dried over $Na_2SO_4$ and evaporated to dryness. The resulting residue was dissolved in 50 ml of chloroform and recrystallized to give 4.5 g, or a 51% yield, of 2-amino-3-cyano-5-chloromethylpyrazine-1-oxide-d3. This light yellow microcrystalline solid had a melting point of 140°–142° C. The IR spectrum of 2-amino-3-cyano-5-chloromethylpyrazine-1-oxide -d3 showed absorptions at 3390–3280, 2240 and 1635 $cm^{-1}$ corresponding to $NH_2$, CN, and C=N signals, respectively. A broad nmr signal for $NH_2$ was observed at 8.10 ppm. The FAB mass spectrum showed a protonated molecular ion peak at m/z 188. This peak confirmed the presence of three deuterium atoms in the molecule. The analogous molecule with no deuterium atoms demonstrated a protonated molecular ion peak at m/z 185.

Synthesis of 2-amino-3-cyano-5-chloromethylpyrazined3

A solution of 2.6 g of 2-amino-3-cyano-5-chloromethylpyrazine-1-oxide-d3 in 100 ml of THF was added dropwise to 5.4 g of phosphorus trichloride while cooled in an ice bath. The solution was stirred for 45 minutes at room temperature. Following evaporation of the solution to a small volume, 100 ml of ice-cold water was added, resulting in the formation of a precipitate. The precipitate was collected by filtration and washed with water to give 1.6 g, or a 70% yield, of 2-amino-3-cyano-5-chloromethylpyrazine-d3, having a melting point of 152°–154° C. The IR spectrum of this compound showed absorptions at 3430–3210 and 2240 cm$^{-1}$ corresponding to $NH_2$ and CN signals, respectively. A broad nmr signal for $NH_2$ was observed at 7.4 ppm.

Synthesis of diethyl N-{[p-N-methyl-N-(2-amino-3-cyano-6-deuteropyrazinyl)-dideuteromethyl]benzoyl} glutamate.

A solution of 2.1 g of potassium carbonate in 30 ml of water was added dropwise with stirring to a solution comprised of 1.9 g of 2-amino-3-cyano-5-chloromethylpyrazine-d3 and 3.36 g of diethyl p-methylaminobenzoyl glutamate in 30 ml of THF at 0°–4° C. Following stirring of the solution at room temperature for an additional hour, 80 ml of water was added, and the mixture was extracted with four 25 ml aliquots of methylene chloride. The extracts were combined, washed with water and dried over $Na_2SO_4$. After the solvent was removed, the residue was redissolved in 10 ml of ethanol and crystallized to give 3.0 g, or a 57% yield, of diethyl-N-(2-amino-3-cyano-5-methylene(d2)-6-deuteropyrazinyl)methylaminobenzoyl]glutamate. This compound had a melting point of 91°–93° C. and an IR spectrum with absorptions at 3350–3330, 1740, and 2240 cm$^{-1}$, corresponding to $NH_2$, C=O, and CN signals, respectively. The nmr spectrum showed signals at 8.10 (1,d,CONH,J=6.7Hz), 7.60 (2,d, arom H, J=9Hz), 7.15 (2, br s, NH2), 6.60 (2,d,arom H,J=9Hz), 4.30 (1,m, NCH), 4.00 (4,q,COOCH2CH3, J=6.7Hz), 3.04 (3,s,N-CH3), 2.32 (2, m, CHCH2CH2), 2.20 (2, m, CH2COO), 1.20 (6, t, CH2CH3, J=6Hz) ppm. The FAB mass spectrum showed a protonated molecular ion peak at m/z 472. This peak indicated that the molecular weight of the compound was 471. The fragment ion at m/z 269 and 240 confirmed the presence of three deuterium atoms, one in the pyrazine ring, and two in the side chain.

Synthesis of diethyl N-[p-[N-(2,4-diamino-7-deutero-6-pteridinyl-9,9-dideuteromethyl)-N-methylamino]-benzoyl]glutamate.

A solution of 0.96 g of guanidine hydrochloride in 50 ml of absolute ethanol was added to a solution of sodium ethoxide prepared by reacting 0.23 g of sodium metal with 50 ml of absolute ethanol. After 15 minutes, the NaCl precipitate was filtered off, and the filtrate was added to 4.5 g of diethyl N-{[p-N-methyl-N-(2-amino-3-cyano-6-deuteropyrazinyl)-dideuteromethyl]benzoyl}glutamate in 100 ml of absolute ethanol. The mixture was refluxed for 1.5 hours, and then 0.2 g of active charcoal was added and hot filtered. The filtrate was refrigerated overnight. The crude product collected was dissolved in a small amount of a 1:4 EtOH-CHCl3 solvent mixture, and was chromatographed on a column of 100 g of silica gel (100–200 mesh, 60 angstroms). The mixture was eluted with the 1:4 EtOH-CHCl3 solvent mixture. The major fraction eluted (R,0.67) gave 2.0 g, or a 40% yield, of diethyl-N-p-[N-(2,4-diamino-7-deutero-6-pteridinyl-9,9-dideuteromethyl)-N -methylamino]benzoyl]glutamate as a TLC-homogeneous bright yellow solid. The IR spectrum of this compound showed absorptions at 3400–3200 and 1750 cm$^{-1}$, corresponding to $NH_2$ and C=O signals, respectively. The nmr spectrum showed signals at 8.25 (1,d,CONH, J=6.6Hz), 7.70 (2,d,arom H,J=9Hz), 7.35 (2,br.s,NH2), 6.80 (2,d,arom H,J=9Hz), 6.60 (2,br,NH2), 4.40 (1,m,NHCH), 4.15 (4,q,COOCH2CH3, J=6Hz), 3.20 (3,s,NCH3), 2.50 (2,m,CH2CH2), 2.10 (2,m, CH2CH2), and 1.20 (6,t,CH2CH3,J=6Hz) ppm. The FAB mass spectrum showed a protonated molecular ion peak at m/z 514 and fragment ions at m/z 351, 311 and 178. This confirmed a molecular weight of the compound of 513, and the presence of three deuterium atoms, one in the pteridine ring, and two in the side chain.

Synthesis of N-[p-[N-(2,4-diamino-7-deutero-6-pteridinyl-dideuteromethyl)-N-methylamino]benzoyl]glutamic acid.

While stirring, 10 ml of 2 M NaOH was added to 0.8 g of diethyl N-[p-[N-(2,4-diamino-7-deutero-6-pteridinyl-9,9-dideuteromethyl)-N-methylamino]-benzoyl]-glutamate dissolved in 100 ml of ethanol. The solution was protected from light, and was stirred for 24 hours at room temperature under $N_2$ gas. The precipitate formed was collected by filtration and was washed with ethanol. The crude sodium salt of N-[p-[N-(2,4-diamino-7-deutero-6-pteridinyldideuteromethyl)-N-methylamino]benzoyl]glutamic acid, or 7,9,9-d3-MTX, was dissolved in 50 ml of water and filtered. The filtrate was acidified to pH 4 with 1 M HCl to give 0.76 g, or a 95% yield, of a bright yellow solid of 7,9,9-d3-MTX. The nmr spectrum showed signals at 8.1 (1,d,CONH,J=6.7Hz), 7.40 (2,br s, NH2), 6.50 (2,br s, NH2), 4.4 (1,m, NCH), 3.20 (3,s, NCH3), 2.40 (2,m, CH2CH2) and 2.10 (2,m, CH2CH2) ppm. The FAB mass spectrum showed a protonated molecular ion peak at m/z 458. This peak indicated that the molecular weight of the compound was 457. Elemental analysis of 7,9,9-d3-MTX confirmed a carbon content of 53.75%, hydrogen content of 5.83%, nitrogen content of 24.19% and oxygen content of 16.23%. Analytical results obtained were within +/− 0.4% of theoretical values.

EXAMPLE 3

To verify that MTX analogs substituted at the 7-position have anticancer activity which is equivalent to or greater than that of MTX, in vitro screening tests were conducted to determine the IC$_{50}$ value for each analog. The IC$_{50}$ value is the drug concentration which inhibits cell growth by 50%.

Two suspensious human leukemia cell lines were employed in this study. The myelogenous leukemia cell line K562 was cultured in RPMI 1640 (JRH Biosciences) containing 10% filtered fetal bovine serum (FBS; Irvine Scientific), and the lymphoblastic leukemia cell line CCRF/CEM was cultured in RPMI 1640 containing 20% FBS, 100 U/ml penicillin (GIBCO Laboratories, Grand Island, NY), and 100 μg/ml streptomycin (GIBCO). Cells were maintained at 37° C. with 5% $CO_2$ in air, and were cultured using standard sterile tissue culture technique.

Prior to toxicity studies, cells were maintained 48 hours in the absence of added inhibitor. Logarithmically growing cells were inoculated at $1\times10^4$ cells/ml in tissue culture grade petri dishes (35×10 mm), and, following a suitable recovery period, were treated with chemical agents. Inhibitor concentrations ranging from $10^{-12}$ to $10^{-4}$ M were added to the cultures except for a control culture, which contained no added drug. Cell counts were performed by hematometer counting during 120 hours of continuous exposure to the drugs. The $IC_{50}$ value was obtained by interpolation from graphs of percent growth inhibition plotted against drug concentration.

$IC_{50}$ values for 7-d-MTX, 7,9,9-$d_3$-MTX and MTX in the two human cell lines are presented in Table 1 and verify the increased anticancer activity of 7-d-MTX as compared with MTX. The $IC_{50}$ values obtained for 7-d-MTX were 15–25% lower than the $IC_{50}$ values obtained for MTX. These results confirm that a lower concentration of 7-d-MTX is needed to effectively impair cancerous growth.

In comparison, the $IC_{50}$ values obtained for 7,9,9-$d_3$-MTX were greater than the $IC_{50}$ values obtained for MTX. This is because the synthesized 7,9,9-$d_3$-MTX product is a D,L-racemate. As confirmed by McGuire et al. (*Biochem. Pharmacol.*, 42, 2400–2403 (1991)), D-enantiomers of analogs of MTX are unlike most other D-enantiomers in that they are capable of exerting growth inhibitory effects, albeit at a substantially lower level than L-enantiomers. Thus, consistent with the results of McGuire et al., the relatively low level of activity of the 7,9,9-$d_3$-MTX D,L-racemate is the result of combination of the lower activity of the D-enantiomer with the higher activity of the L-enantiomer to produce lower overall biological activity.

TABLE 1

Anticancer activity of 7-d-MTX and 7,9,9-$d_3$-MTX as compared with MTX

| Compounds | $IC_{50}$ (nM) | |
|---|---|---|
| | K562 Cells | CCRF/CEM Cells |
| 7-d-MTX | 6 | 9.5 |
| 7,9,9-$d_3$-MTX | 40 | 48.0 |
| MTX | 8 | 11.3 |

EXAMPLE 4

To verify that MTX analogs substituted at the 7-position are comparable to MTX in their ability to inhibit DHFR, tests were conducted to determine the $ID_{50}$ value for each analog. The $ID_{50}$ value is the drug concentration which inhibits enzyme activity by 50%.

The ability of 7-d-MTX and 7,9,9-$d_3$-MTX to inhibit DHFR isolated from chicken liver and *L. casei* were investigated and compared with the ability of MTX to inhibit DHFR. Inhibition of DHFR by was evaluated by means of a spectrophotometric assay using the parent drug, MTX, as a control. DHFR activity was measured as the decrease over time in absorbance at 340 nm.

For this assay, 1.0 ml of an assay solution consisting of 50 mM potassium phosphate (pH 7.0), 0.1 mM dihydrofolate, 0.1 mM NADPH, 0.02 units of DHFR from chicken liver or 0.03 units of DHFR from *L. casei*, and containing concentrations of 7-d-MTX, 7,9,9-$d_3$-MTX or MTX ranging from $10^{-9}$ to $10^{-6}$ M was employed. DHFR was diluted prior to each experiment in 50 mM potassium phosphate buffer (pH 7.0) containing 0.1 mM NADPH and 0.1% BSA.

Inhibition studies were carried out by adding to a 1.0 ml cuvette the assay solution containing all components except dihydrofolate, and incubating 2 minutes at room temperature. The absorbance of the solution at 340 nm was recorded immediately following the addition of dihydrofolate. The mixtures were then incubated at room temperature for 5 minutes, and the absorbance at 340 nm was again recorded. The enzyme activity was calculated as the change in absorbance at 340 nm over time, and was expressed as the percentage of activity obtained in the absence of 7-d-MTX, 7,9,9-$d_3$-MTX or MTX. $ID_{50}$ values were determined by interpolation from graphs of percent of inhibition plotted against drug concentration.

$ID_{50}$ values for 7-d-MTX, 7,9,9-$d_3$-MTX and MTX against DHFR obtained from two different sources are presented in Table 2. These values verify the increased anticancer activity of 7-d-MTX as compared with MTX. The $ID_{50}$ values obtained for MTX were about 25% higher than the $ID_{50}$ values obtained for 7-d-MTX. These results confirm that a lower concentration of 7-d-MTX is needed to inhibit DHFR. In comparison, a higher concentration of 7,9,9-$d_3$-MTX was needed to inhibit DHFR, which appeared to be the result of combination of the lower activity of the D-enantiomer with the higher activity of the L-enantiomer to produce lower overall biological activity for the D,L-racemate, as was observed in Experiment 3.

TABLE 2

Inhibition of DHFR by 7-d-MTX as compared with MTX

| Compounds | $ID_{50}$ (nM) | |
|---|---|---|
| | Chicken Liver DHFR | *L. casei* DHFR |
| 7-d-MTX | 50 | 86 |
| 7,9,9-$d_3$-MTX | 120 | 114 |
| MTX | 63 | 106 |

EXAMPLE 5

To confirm that the decreased rate of metabolism of 7-d-MTX and 7,9,9-$d_3$-MTX as compared with MTX is due to deuterium-mediated inhibition of hydroxylation at the 7-position of the pteridine ring, the metabolism of these inhibitors in rabbit liver was investigated. The half-lives of the inhibitors, or the time needed for each inhibitor concentration to decrease by half, as well as their rate of formation of 7-OH-MTX, were determined.

For these experiments, freshly isolated liver from a New Zealand white rabbit was homogenized in 400 ml of cold buffer of pH 7.6 consisting of 10 mM Tris-HCl, 25 mM sucrose and 10 mM $MgCl_2$. The homogenate was centrifuged at 1000× g for 20 minutes at 4° C. and the resulting pellet was resuspended in about 14 ml of the same buffer. One ml of a 0.5 mg/ml solution of either MTX or 7-d-MTX was added, and the homogenate was incubated at 37° C. in a shaking water bath. Two ml samples of the homogenate were removed at 10 minute intervals. Samples were boiled 5 minutes to denature proteins, and then centrifuged to pellet cell debris. To determine inhibitor and 7-OH-MTX levels, 100 μl of the supernatant was analyzed by HPLC. For HPLC analysis, a Perkin-Elmer 410 LC solvent delivery system and a 5-μm IBM ODS column (4.1×250 mm) with a $C_{18}$ Guard column were employed. The mobile phase consisted of 0.1 M monobasic sodium phosphate and 0.1 M Tris-HCl in 27% methanol at a final pH of 7.6. The eluate was monitored at 315 nm with a LC 90 UV variable-wavelength detector using a flow rate of 1.5 ml/minute. Detector output was recorded and integrated by a Perkin-Elmer LCI 100 integrator.

Results presented in Table 3 confirm the longevity of 7-d-MTX as compared with MTX. The half-life for 7-d-MTX is about 60% greater than the half-life for MTX. This verifies that 7-d-MTX is broken down much less rapidly than MTX.

TABLE 3

Half-Life of 7-d-MTX as compared with MTX

| Exp. No. | Half-Life (hr) | | |
|---|---|---|---|
| | 7-d-MTX | MTX | 7-d-MTX/MTX |
| 1 | 1.36 | 0.87 | 1.56 |
| 2 | 0.81 | 0.47 | 1.72 |
| 3 | 0.57 | 0.31 | 1.83 |
| 4 | 0.58 | 0.42 | 1.38 |
| 5 | 0.68 | 0.47 | 1.45 |
| Mean +/− SD | | | 1.59 +/− 0.19 |

In the same experiment, the deuterium-mediated inhibition of hydroxylation at the 7-position of the pteridine ring of MTX was investigated. The experimental results are set out in Table 4.

The decreased rate of formation of 7-OH-MTX from 7-dMTX as compared to that from MTX is indicated in Table 4 by the lower levels of 7-OH-MTX converted from 7-d-MTX as a function of time. Per unit time, about 70% less 7-OH-MTX is formed from 7-d-MTX than from MTX. These results confirm that deuteration at the 7-position of MTX impedes formation of 7-OH-MTX. Similar results were obtained for 7,9,9-d$_3$-MTX.

TABLE 4

Rate of formation of 7-OH-MTX from 7-d-MTX as compared with from MTX

| Exp. No. | 7-OH-MTX Conversion (μg/ml) (h) | | |
|---|---|---|---|
| | 7-d-MTX | MTX | 7-d-MTX/MTX |
| 1 | 6.59 | 9.52 | 0.69 |
| 2 | 6.13 | 9.78 | 0.63 |
| 3 | 13.72 | 20.7 | 0.66 |
| 4 | 10.21 | 14.58 | 0.70 |
| 5 | 12.13 | 16.52 | 0.73 |
| Mean +/− SD | | | 0.69 +/− 0.04 |

EXAMPLE 6

To further confirm that the decreased rate of metabolism of 7-d-MTX as compared with MTX is due to deuterium-mediated inhibition of hydroxylation at the 7-position of the pteridine ring, the metabolism of 7-substituted analogs of MTX was investigated in vivo. Since the MTX analogs of the present invention both reduce hydroxylation at the C-7 position and demonstrate similar properties, 7,9,9-d$_3$-MTX was employed as a representative 7-substituted MTX analog in this example.

For these experiments, 20 mg of NaHCO$_3$ and either 7,9,9-d$_3$-MTX or MTX were dissolved in 5 ml of sterile saline for intravenous administration. A male New Zealand White rabbit was cannulated through the middle ear artery. A single bolus 16.7 mg/kg dose of drug was administered into the ear vein, and 1.0 ml blood samples were withdrawn from the cannulated artery into heparinized tubes at 0, 5, 15, 30, 45, 60, 75 and 90 minutes following drug administration. Plasma was separated from the samples by centrifugation at 1000 rpm, and was kept frozen until analysis. HPLC analysis was used to monitor the concentration of added drug or newly formed 7-OH-MTX in each of the samples.

HPLC analysis was performed as in Example 5, with the exception that the mobile phase was 0.1 M monobasic sodium phosphate and 0.1 M Tris-HCl in 20% methanol at a final pH of 6.7. p-Aminoacetophenone (10 μg/ml in water) was used as an internal standard. Retention times for MTX, 7-OH-MTX and p-aminoacetophenone were 9.1, 11.26 and 14.5 minutes, respectively. 7,9,9-d$_3$-MTX demonstrated the same retention time as did MTX.

Pharmacokinetic parameters were determined by the method of residual, a standard pharmacokinetic technique for resolving a curve into its various exponential components. The area under the plasma drug concentration-time curves for 7,9,9-d$_3$-MTX, MTX, 7-OH-MTX formed from 7,9,9-d$_3$-MTX, and 7-OH-MTX formed from MTX indicated the total amount of each drug in vivo within 1.5 hours. The elimination rate constant of 7-OH-MTX formed from 7,9,9-d$_3$-MTX or MTX was determined from linear regression of the terminal concentration-time data.

For the formation of 7-OH-MTX, the time needed to reach maximum concentration, $t_{max}$, is independent of the amount of 7-OH-MTX formed, and is dependent on the rate constant, $k_a$, for hydroxylation of 7,9,9-d$_3$-MTX or MTX, as well as elimination, $k_e$, of 7-OH-MTX formed from 7,9,9-d$_3$-MTX or MTX. Thus $t_{max}$ was calculated according to the formula:

$$t_{max} = 2.3 \log (k_a/k_e)/(k_a/k_e)$$

The results are set forth in Table 5 and verify that deuterium-mediated inhibition of hydroxylation at the 7-position of the pteridine ring of MTX occurs in vivo.

The decreased formation of 7-OH-MTX from 7,9,9-d$_3$-MTX as compared with that from MTX is indicated in the first column of Table 5 by the substantially lower level of 7-OH-MTX converted from 7,9,9-d$_3$-MTX as a function of time as compared with level of 7-OH-MTX converted from MTX. The peak level of 7-OH-MTX obtained from 7,9,9-d$_3$-MTX was about 70% less than the peak level of 7-OH-MTX obtained from MTX. Additionally, it took more than twice as long to achieve this peak level with the administration of 7,9,9-d$_3$-MTX as compared to that of MTX.

These results clearly verify that substitution at the 7-position of MTX impedes formation of 7-OH-MTX in vivo as well as in vitro.

TABLE 5

Pharmacokinetic parameters of 7-OH-MTX formed from either 7,9,9-d$_3$-MTX or MTX

| | 7-OH-MTX conversion (μM) (min) (+/− SD) | 7-OH-MTX Peak Level (μM +/− SD) | 7-OH-MTX Time to Peak (min +/− SD) |
|---|---|---|---|
| 7,9,9-d$_3$-MTX (n = 7) | 2295.4 +/− 1091.2 | 37.03 +/− 10 | 18.05 +/− 2.8 |
| MTX (n = 4) | 3375.1 +/− 1378.2 | 55.56 +/− 20 | 7.96 +/− 1 |

All the references cited herein are hereby incorporated in their entireties by reference.

While this invention has been described with an emphasis upon preferred embodiments, it will be obvious to those of ordinary skill in the art that variations in the preferred compounds and methods may be used and that it is intended that the invention may be practiced otherwise than as specifically described herein. Accordingly, this invention includes all modifications encompassed within the spirit and scope of the invention as defined by the following claims.

What is claimed is:

1. A compound having the formula:

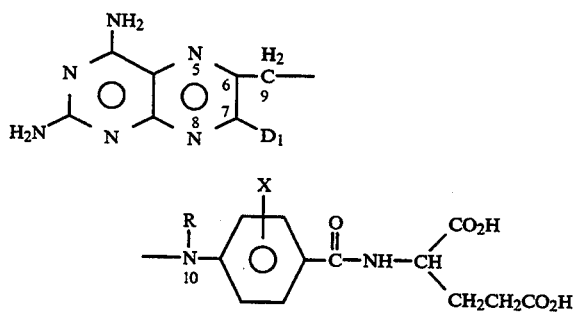

wherein R is methyl or hydro, $D_1$ is deutero, and X is halo or hydro, and therapeutically acceptable salts thereof.

2. The compound of claim 1 wherein R is hydro.
3. The compound of claim 1 wherein R is methyl.
4. The compound of claim 1, wherein said compound has the formula:

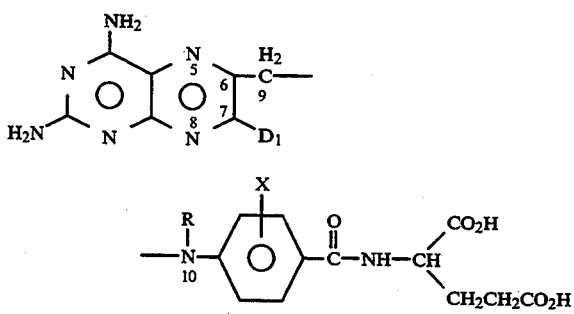

wherein R is methyl or hydro, $D_1$ is deutero, and X is hydro.

5. The compound of claim 4 wherein R is hydro.
6. The compound of claim 4 wherein R is methyl.
7. The compound of claim 6 wherein said compound is 7-d-MTX.
8. A pharmaceutical composition comprising a pharmaceutically acceptable excipient and a therapeutically effective amount of a compound of claim 2.
9. A pharmaceutical composition comprising a pharmaceutically acceptable excipient and a therapeutically effective amount of a compound of claim 3.
10. The method of using the compound of claim 1 in treating cancer capable of being effectively treated by MTX.
11. The method of using the compound of claim 2 in treating cancer capable of being effectively treated by MTX.
12. The method of using the compound of claim 3 in treating cancer capable of being effectively treated by MTX.
13. The method of using the compound of claim 1 in treating cancer capable of being effectively treated by MTX.
14. The method of using the compound of claim 5 in treating cancer capable of being effectively treated by MTX.
15. The method of using the compound of claim 6 in treating cancer capable of being effectively treated by MTX.
16. The method of using the compound of claim 7 in treating cancer capable of being effectively treated by MTX.
17. A pharmaceutical composition comprising a pharmaceutically acceptable excipient and a therapeutically effective amount of a compound of claim 4.
18. A pharmaceutical composition comprising pharmaceutically acceptable excipient and therapeutically effective amount of a compound of claim 1.
19. A pharmaceutical composition comprising pharmaceutically acceptable excipient and therapeutically effective amount of a compound of claim 5.
20. A pharmaceutical composition comprising pharmaceutically acceptable excipient and therapeutically effective amount of a compound of claim 6.
21. A pharmaceutical composition comprising pharmaceutically acceptable excipient and therapeutically effective amount of a compound of claim 7.

* * * * *

UNITED STATES PATENT AND TRADEMARK OFFICE
CERTIFICATE OF CORRECTION

PATENT NO. : 5,382,582
DATED : JANUARY 17, 1995
INVENTOR(S) : CARCY L. CHAN

It is certified that error appears in the above-identified patent and that said Letters Patent is hereby corrected as shown below:

ON THE TITLE PAGE:

[56] References Cited

OTHER PUBLICATIONS, 2nd page, first column, line 5, delete "Methylmethotrexate" and substitute therefor -- methylmethotrexate --; and 2nd page, first column, line 28, delete "hydrosy" and substitute therefor -- hydroxy --.

Column 1, after title, insert as separate paragraph

-- STATEMENT AS TO RIGHTS TO INVENTIONS
MADE UNDER FEDERALLY SPONSORED
RESEARCH AND DEVELOPMENT

This invention was made with government support, Grant No. S06GM08177, awarded by the National Institutes of Health. The government may have certain rights in this invention. --;

UNITED STATES PATENT AND TRADEMARK OFFICE
CERTIFICATE OF CORRECTION

PATENT NO. : 5,382,582

DATED : JANUARY 17, 1995

INVENTOR(S) : CARCY L. CHAN

It is certified that error appears in the above-identified patent and that said Letters Patent is hereby corrected as shown below:

Column 1, line 25, delete "diamino-6pteridinyl" and substitute therefor -- diamino-6-pteridinyl --;

Column 1, line 26, delete "glutamicacid" and substitute therefor -- glutamic acid --;

Column 4, line 55, delete "$D_1$ position" and substitute therefor -- C-7 position --;

Column 6, lines 28-29, "4-amino" should read -- 2,4-diamino --;

Column 6, line 45, delete "chloropyruvaldoximed-4" and substitute therefor -- chloropyruvaldoxime-d4 --;

Column 6, lines 59 and 61, "2,4 diamino" should read -- 2,4-diamino --;

Column 11, lines 5, 29 and 61; Column 12, lines 22 and 61, and; Column 14, line 36, delete "$cm^1$" and substitute therefor -- $cm^{-1}$ --;

Column 12, line 1, "4-amino-" should read -- 2,4-diamino --;

Column 12, line 9, "2-amino-3-cyano-6 dueteropyrazin" should read -- 2-amino-3-cyano-6-deuteropyrazin --;

UNITED STATES PATENT AND TRADEMARK OFFICE
CERTIFICATE OF CORRECTION

PATENT NO. : 5,382,582
DATED : JANUARY 17, 1995
INVENTOR(S) : CARCY L. CHAN

It is certified that error appears in the above-identified patent and that said Letters Patent is hereby corrected as shown below:

Column 12, line 18, "4-amino" should read -- 2,4-diamino --;

Column 12, line 36, "4-amino" should read -- 2,4-diamino --;

Column 12, line 39, "triethylamino" should read -- triethylamine --;

Column 12, line 44, "diethyl-L-glutamate" should read -- diethyl L-glutamate --;

Column 12, line 65, delete the second occurrence of "m";

Column 14, line 12, "14 2" should read -- 14.2 --;

Column 15, line 2, "chloromethylpyrazined3" should read -- chloromethylpyrazine-d3 --;

Column 15, line 34, "diethyl-N-" should read -- diethyl N- --;

Column 15, line 36, after "C." insert -- , --;

Column 16, line 3, "diethyl-N-" should read -- diethyl N- --;

Column 17, line 56, delete "by";

UNITED STATES PATENT AND TRADEMARK OFFICE
CERTIFICATE OF CORRECTION

PATENT NO. : 5,382,582
DATED : JANUARY 17, 1995
INVENTOR(S) : CARCY L. CHAN

It is certified that error appears in the above-identified patent and that said Letters Patent is hereby corrected as shown below:

Column 19, line 27, "7-dMTX" should read -- 7-d MTX --; and

Column 20, line 31, "$t_{max} = 2.3 \log (k_a / k_e) / (k_a / k_e)$" should read -- $t_{max} = 2.3 \log (k_a / k_e) / (k_a - k_e)$ --.

Column 22, line 19, delete "1" and substitute therefor -- 4 --;

Column 22, lines 34, 37, 40, and 43, after "comprising" insert -- a --; and

Column 22, lines 35, 38, 41, and 44, after "excipient and" insert -- a --.

Signed and Sealed this

Fifth Day of September, 1995

Attest:

BRUCE LEHMAN

*Attesting Officer*    *Commissioner of Patents and Trademarks*